(12) United States Patent
Gramann et al.

(10) Patent No.: US 6,946,864 B2
(45) Date of Patent: Sep. 20, 2005

(54) METHOD FOR MEASURING PRODUCT PARAMETERS OF COMPONENTS FORMED ON A WAFER AND DEVICE FOR PERFORMING THE METHOD

(75) Inventors: Wolfgang Gramann, Regensburg (DE); Raimund Oberschmid, Sinzing (DE); Werner Späth, Holzkirchen (DE); Wolfgang Teich, Regensburg (DE)

(73) Assignee: Osram GmbH, Munich (DE)

( * ) Notice: Subject to any disclaimer, the term of this patent is extended or adjusted under 35 U.S.C. 154(b) by 497 days.

(21) Appl. No.: 10/078,146

(22) Filed: Feb. 19, 2002

(65) Prior Publication Data

US 2002/0166777 A1 Nov. 14, 2002

Related U.S. Application Data

(60) Provisional application No. 60/357,306, filed on Feb. 15, 2002.

(30) Foreign Application Priority Data

Feb. 19, 2001 (DE) .......................... 101 07 689

(51) Int. Cl.[7] ............................................. G01R 31/28
(52) U.S. Cl. ......................... 324/765; 324/752; 324/757
(58) Field of Search ........................ 3324/752; 324/754, 324/755, 757, 758, 765

(56) References Cited

U.S. PATENT DOCUMENTS

| 4,168,212 A | | 9/1979 | Faktor et al. |
| 4,521,730 A | * | 6/1985 | Shulman .................... 324/754 |
| 5,287,169 A | | 2/1994 | Pollak et al. |
| 5,358,417 A | * | 10/1994 | Schmedding ............... 439/178 |
| 5,639,343 A | | 6/1997 | Dobkin |
| 5,969,534 A | * | 10/1999 | Hubner et al. .............. 324/757 |
| 6,074,546 A | | 6/2000 | Sun et al. |

FOREIGN PATENT DOCUMENTS

EP      0 400 387 A2     12/1990

OTHER PUBLICATIONS

"Diode Laser Material Evaluation using Liquid Contact Luminescence" (Zory et al.), IEEE 1995, Proceedings of LEOS 95, pp. 133–34, Month unavailable, 1995.
"Internal Quantum Efficiency Measurements of GAINP Quantum Well Laser Material Using Liquid Contact Luminescence" (Hsu et al.), Proceedings of Conference Laser Diodes and Applications, PIE, month unavailable, 1996, pp. 136–143.
"Liquid Contact Luminescence for Laser Material Evaluation and Flat Panel Display" (Largent et al.), Proceedings of LEOS 97, IEEE 1997, pp. 107–108, month unavailable 1997.

* cited by examiner

*Primary Examiner*—Ernest Karlsen
(74) *Attorney, Agent, or Firm*—Laurence A. Greenberg; Werner H. Stemer; Ralph E. Locher (57) ABSTRACT

A measuring arrangement for measuring product parameters of a component in the epitaxial layer (28) of a wafer comprises measuring probe (3) on whose contact side (23) a recess (24) is installed, into which an electrolyte can be poured. The electrolyte produces an electrical connection between a contact body (11), which is charged with a signal from a pulsed-current source, and the surface (22) of the wafer (2). A detector (16) serves for detecting the light which is emitted by the component.

20 Claims, 5 Drawing Sheets

FIG 8

METHOD FOR MEASURING PRODUCT PARAMETERS OF COMPONENTS FORMED ON A WAFER AND DEVICE FOR PERFORMING THE METHOD

This application claims priority from Provisional Application Ser. No. 60/357,306, filed 15 Feb. 2002.

BACKGROUND OF THE INVENTION

FIELD OF THE INVENTION

The present invention relates to a method for measuring product parameters of components on a wafer whereby, with the aid of a measuring probe which is placed on a wafer contact region, the component is charged with an electrical signal from a contact of said probe.

The invention also relates to a device for measuring product parameters of a component on a wafer by means of a measuring probe on a contact side of which is a probe contact that is chargeable with an electrical signal.

According to a method that is known from prior art, a measurement probe is placed onto a wafer contact region, and the component is charged with an electrical signal via a probe contact. In order to achieve effective contact between the wafer contact region and the measurement probe, it is generally necessary to produce a bond connection between the probe contact and the wafer contact region. At the very least, it is necessary to realize the wafer contact region as a contact layer on the wafer. But this requires additional processing steps, which delays the measurement of the epitaxy layers beneath the contact layer.

In other known measuring methods, the wafers are individualized into components, and the actual measuring method is carried out on individual components.

According to another known method, for optoelectronic components the emission wavelength with the maximum emission and the efficiency of the electroluminescence are determined with the aid of the photoluminescence. But this technique gives only estimated values. It is even impossible to predict the order of magnitude.

Furthermore, a disadvantage of all known methods is that the measurement of the wafers requires several days in practice, and thus the epitaxy process cannot be controlled according to the results of the measurements. Besides, it has been possible to determine the ESD stability and aging behavior only of individualized components.

SUMMARY OF THE INVENTION

Taking this prior art as a starting point, the invention is based on the object of laying out a method for analyzing components on a wafer in a non-destructive fashion.

This object is inventively achieved in that the electrical connection between the wafer and the measuring probe is produced with the aid of an electrolyte which is interposed between the wafer contact region and the probe contact.

The invention is also based on the object of creating a device with which product parameters of components on a wafer can be measured in a non-destructive fashion.

This object is inventively achieved in that the probe contact is set back from the contact side, and that a recess that can be filled with an electrolyte is arranged on the contact side extending to the probe contact.

Owing to the presence of the electrolytes, a substantially uniform current density across the wafer contact region is possible. Conversely, without electrolytes the probe contact would have to touch the wafer contact region directly. In that case, contact between the contact surface and the wafer contact region would only exist in certain points on a microscopic scale, owing to the roughness of the surface of the wafer contact region and the probe contact. As a result, current contractions would occur, which would cause localized melting of the wafer contact region. Furthermore, voltage sparkovers can occur, along with the associated current surges. Because the electrolyte also enters fine depressions of the wafer contact region and the measuring probe, the connection which is produced between the wafer contact region and the probe contact conducts effectively over a large area. Therefore, current contractions do not occur. And furthermore, there is no risk of voltage sparkovers.

A suitable device for carrying out the proposed method thus comprises a contact surface which is set back relative to the wafer contact region and which adjoins a recess which recedes from the contact side of the measuring contact. The electrolyte which produces the electrical connection between the wafer contact region and the probe contact can be inserted into the recess.

Additional preferred embodiments are subject matter of the subclaims.

The invention will now be described in detail in connection with the enclosed drawings.

DESCRIPTION OF THE PREFERRED EMBODIMENTS

Figure 1:
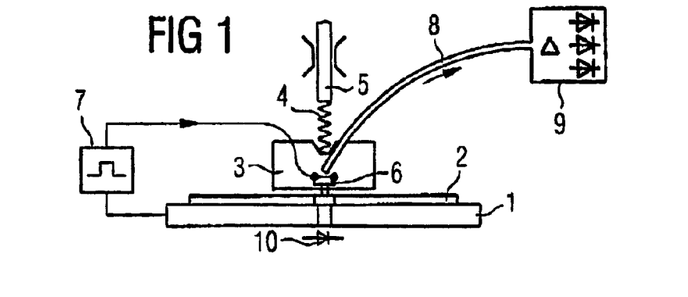
FIG. 1: a side view of a measuring arrangement.

FIG. 1 represents a measuring arrangement comprising a wafer 2 on a carrier 1. In contact with the wafer 2 is a measuring probe 3, which is pressed by means of a compression spring 4 and a guide 5 onto the contact region, which is allocated to a component, of the wafer 2. The component can be an opto-electronic component, for instance an LED. In the measuring probe 3 is a measuring mechanism 6, which is connected to a pulsed-current source 7. The pulsed-current source 7 is also connected to the carrier 1.

An optical fiber 8 leading to a detector 9 is provided for detecting the light which is emitted by components on the wafer 2. A detector 10 for detecting the radiation emitted by the component may also be disposed on the side of the carrier 1 which is averted from the measuring probe 3. To this end, a feed-through is installed in the carrier 1, which allows the emitted light to reach the detector 10 through the wafer 2. Preferably, the detector 9 can also be a spectrometer which is suitable for the simultaneous pick-up of the whole spectrum of a single light pulse or only a few light pulses. The spectrometer can comprise a diffraction grid with a detector array or in the simplest case two detectors in front of which filters with different spectral sensitivities are arranged. In this case, an average wavelength can be determined from the signal ratio of the two detectors.

Lastly, the detector 10 can also comprise a plurality of isolated single detectors, potentially including a lens which refracts the luminance image. Generally, the detector comprises a detector array such as a CCD camera with which the radiation distribution in the component can be determined. This type of detector 10 thus gives information about the current distribution in the component and the scatter effect of the layer boundary surfaces and surfaces of the wafer 2.

Furthermore, for transparent wafers the detector 10 can also be an optical fiber connected to a spectrometer, as described in connection with detector 9.

Figure 2:
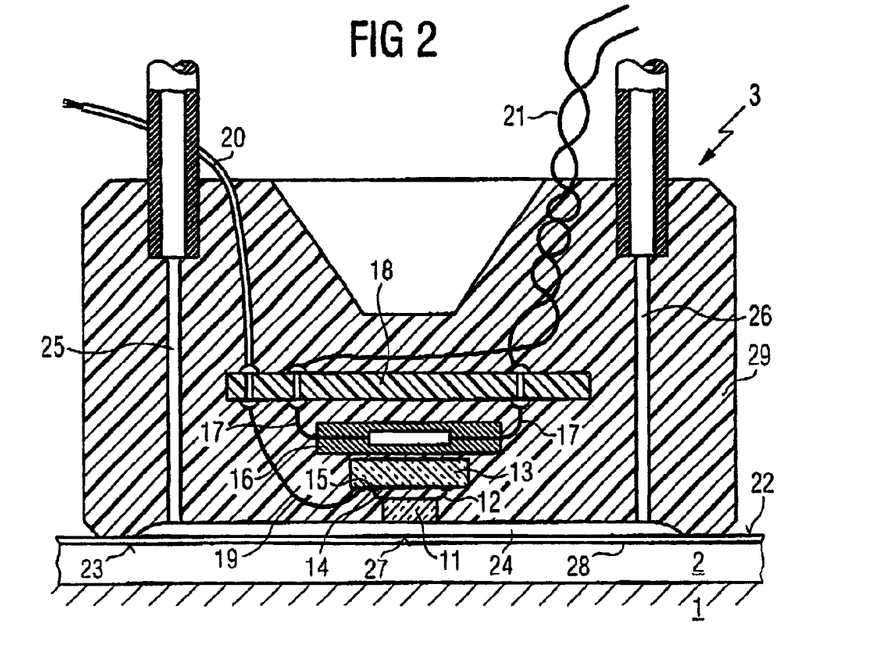
FIG. 2: an enlarged cross-sectional view through the measuring probe of the measuring arrangement from FIG. 1.

FIG. 2 represents a cross-section through the measuring probe 3 from FIG. 1. The measuring device 6 in the probe 3 is provided with a contact body 11, which is produced from an optically conductive and transparent material. The conductivity of the contact body 10 should be greater than $10^{-3}$ $\Omega^{-1}cm^{-1}$. For example, doped SiC can be utilized for the contact body 11 if the measuring arrangement is utilized for visible to infrared light. Typically, the contact body has a dimension of 500 $\mu$m×500 $\mu$m and a thickness of approx. 200 $\mu$m. The contact body 11 is connected to a glass lamella 13 via bonding wires 12, which are fixed to interconnects 15 on its contact side 14 facing contact body 11.

Located behind the glass lamella 13 is a detector 16, which can detect the light passing through the contact body 11 and the glass lamella 13. The detector 16 is connected to a printed board 18 via bonding wires 17. The interconnects 15 on the glass lamella 13 are also connected to the printed board 18 via bonding wires 19. From there, lines 20 lead to the pulsed-current source 7, and lines 21 lead to evaluating electronics, which are not represented. Thus, the measuring probe 3 represented in FIG. 2 does not require optical fiber 8.

The contact body 11 is arranged in the measuring probe 3 at a distance from the surface 22 of the wafer 2. To accomplish this, a recess 24 is fashioned on a contact side 23 of the measuring probe 3, which can be filled with an electrolyte via a supply line 25. The electrolyte can be extracted from the recess 4 via a drain line 26. The electrolyte is preferably a highly photoconductive and chemically non-aggressive electrolyte such as a saline solution on an $MgCl_2$ or NaCl basis. Other electrolytes, for instance $MgCl_2$, $NH_4Cl$, or $Na_2SO_4$, have also been successfully tested. Any type of electrolyte with sufficient electrical conductivity and sufficient transparency in the respective wavelength band is presumed suitable for the measuring arrangement. Lastly, the electrolytes should therefore be selected according to their compatibility with subsequent steps for processing the wafer 2. The compatibility of the electrolyte with subsequent processing steps is particularly crucial when slight residual contaminations of the wafer 2 by the electrolytes remain at the conclusion of the measuring procedure.

By virtue of the electrolytes, a uniform current density emerges with respect to the contact body 11 and a wafer contact region 27 of a component which is formed in an epitaxial layer 28 of the wafer 2. The presence of the electrolyte prevents current contractions in the current transition from the contact body 11 to the wafer contact region 27 of the component. Consequently, the surface 22 does not melt. In order to guarantee a homogenous distribution of the current coming from the contact body 11, the thickness of the electrolyte layer must be large enough to compensate roughnesses of the surface 22 and the contact body 11. Practice has shown that the thickness of the electrolyte layer must be at least 5 $\mu$m.

The effective electrolytic contact surface area on the wafer 2 is preferably selected according to the dimension of the subsequent component. The effective electrolytic contact surface area is usually between 0.1 mm×0.1 mm and 1 mm×1 mm.

Figure 3:
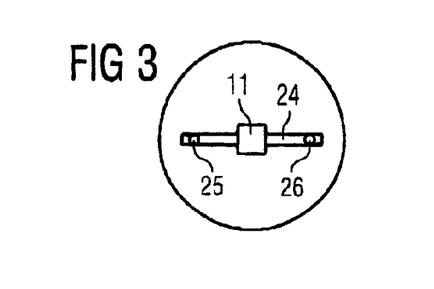
FIG. 3: a plan view of the measuring probe from FIG. 2, from below.

FIG. 3 is a plan view of the measuring probe 3 from FIG. 2 from below. At center note contact body 11, from which the recess 24 extends in the lateral direction. Also visible in FIG. 3 are the openings of supply line 25 and drain line 26. Both the recess 24 and the supply line 25 and drain line 26 are realized in a plastic body, which also surrounds the measuring device 6.

Figure 4:
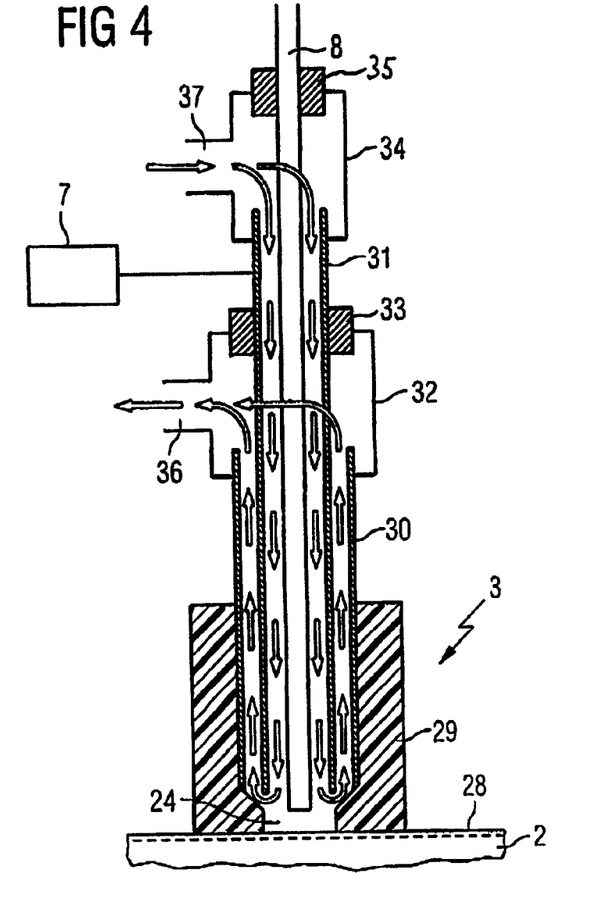
FIG. 4: a cross-section through a modified measuring arrangement.

FIG. 4 represents a modified measuring probe 3 in cross-section. The representation is not true to scale. The measuring probe 3 in FIG. 4 comprises an outer tube 30, which is inserted in the plastic body 29 and in which an inner tube 31 is disposed. Inside the inner tube 31 is the optical fiber 8. The outer tube 30 has a length which is smaller than the length of the inner tune 31. A T-flange 32 is arranged at the end of the outer tube 30 which is averted from the wafer 2. The T-flange 32 has a seal 33 through which the inner tube 31 extends. The end of the inner tube 31 which is averted from the wafer likewise terminates with a T-flange 34, which comprises a seal 35 through which the optical fiber 8 extends. Both the T-flange 32 and the T-flange 34 comprise lateral spigots 36 and 37, through which an electrolyte can be introduced into the recess 24. In the measuring probe 3 represented in FIG. 4, the inner tube 31 has the same function as the contact body 11 in the measuring probe 3 represented in FIG. 2. The inner tube 31 is thus also connected to the pulsed-current source 7 at its top end.

Figure 5:
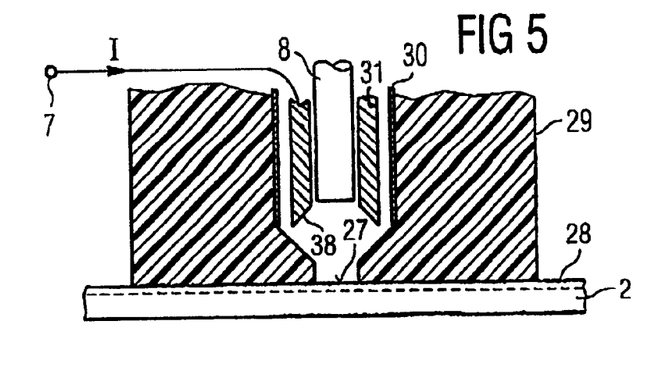
FIG. 5: an enlarged cross-section through the measuring arrangement from FIG. 4.

FIG. 5 represents the bottom end of the inner tube 31 in an enlarged perspective. At the end of the inner tube 31, end faces 38 of the inner tube 31 are tapered inward. The end faces 38 are expediently produced by boring the inner tube 31 along its longitudinal axis. An insulating guard layer, for instance an oxide layer, is also removed in this process. Through the beveled and thus wide end faces 38 the current can enter the electrolyte 24, and in the electrolyte it can reach the surface 22 of the wafer 2. The radiation emitted in the contact region 27 of the wafer 2 can then be detected by the optical fiber 8.

Figure 6:
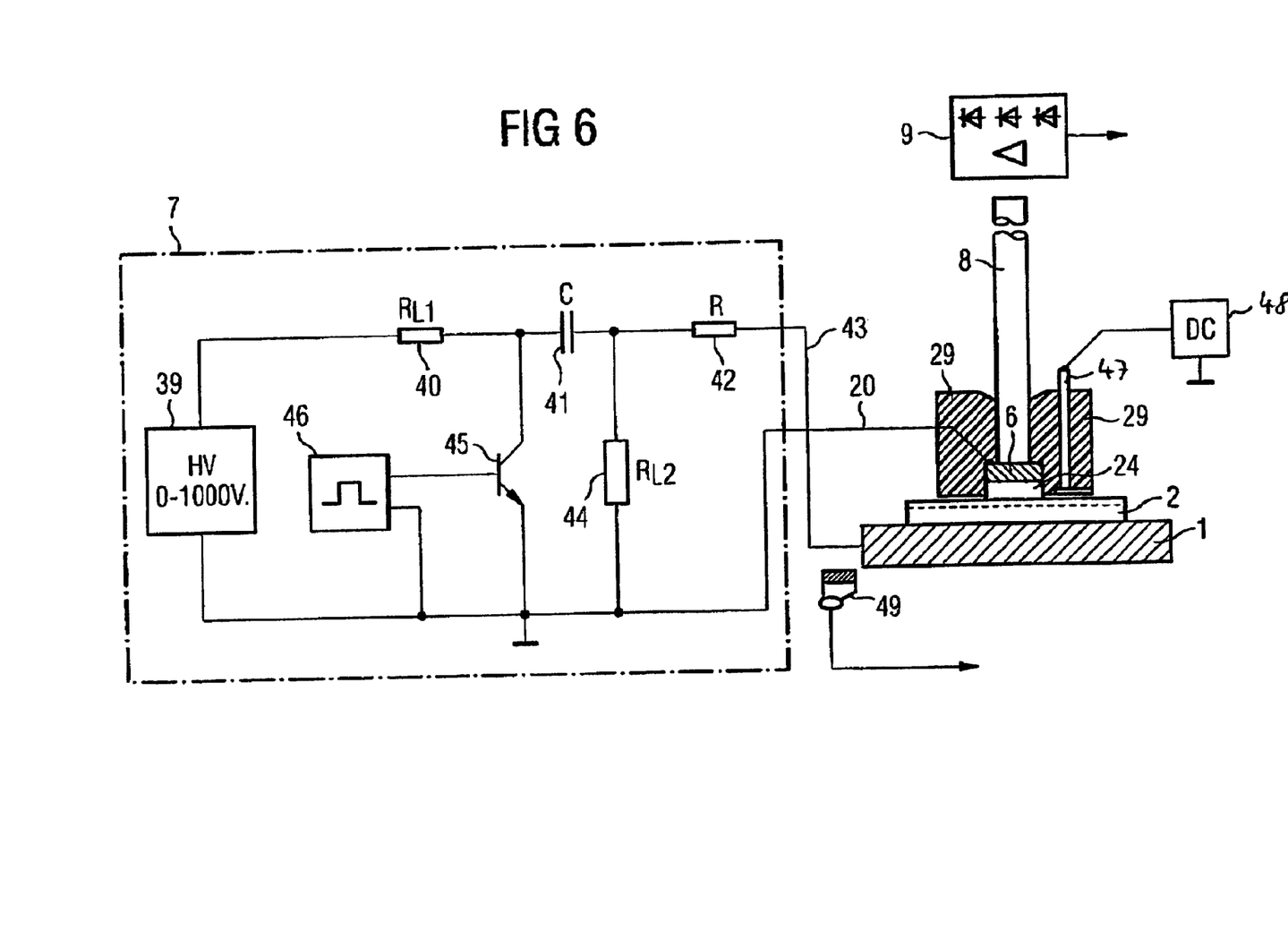
FIG. 6: an exemplifying embodiment of a pulsed-current source, and a cross-section through another modified measuring arrangement.

FIG. 6 represents a possible circuit for the pulsed-current source 7. The pulsed-current source 7 is provided with a high-voltage supply 39, which is connected to a coupling capacitor 41 via a load resistor 40. The coupling capacitor 41 is connected to the carrier 1 of the measuring arrangement via a dropping resistor 42 and a signal line 43. The signal line 43 is connected to the carrier 1 in order to prevent cross-talk of the current signal onto the measuring device 6. The line 20 leading from the measuring device 6 ultimately leads back to the pulsed-current source 7, where it is connected to ground. Connected parallel to the measuring probe 3 is a second load resistor 44. In addition, a transistor 45, which is controlled by a pulse generator 46, is connected parallel to the high-voltage supply 39.

Typically, a value of 1 M$\Omega$ is selected for the first load resistor 40; a value of 2 k$\Omega$ is selected for the dropping resistor 42; and a value of 1 MΩ is selected for the second load resistor 44. The coupling capacitor 41 typically has a value of 3 nF.

The transistor 45 serves to charge and discharge the coupling capacitor 41. The time constant for the charging process is determined by the value of the coupling capacitor 41 and the value of the first load resistor 40. On the other hand, the time constant for the discharge process is determined by the value of the coupling capacitor 41 and the value of the dropping resistor 42. The resistance of the electrolyte in the recess 24 typically equals approx. 50Ω and is thus negligible compared to the dropping resistor 42. The second load resistor 44 ultimately serves to charge the capacitor 41 even when the measuring probe 3 has been taken off.

Overall the pulsed-current source 7 has a high resistance, which is between 100 and 10 kΩ. The pulsed-current source emits single pulses or pulse sequences interrupted by long pauses, the period of the individual pulses being typically between 0.1 μs and 1 ms. However, the total charge of the single pulses or pulse sequences which are emitted by the pulsed-current source 7 should remain under 1 mAs in order to prevent the onset of electrochemical processes at the surface 22 of the wafer 2 and on the side of the contact body 11 or inner tube 31 facing the wafer. If the electromagnetic processes at the surface 22 of the wafer 2 are negligible, other high-voltage pulse sources can be utilized in connection with the dropping resistor 42. What is essential is that the high-voltage pulse source have a high internal resistance. The internal resistance should be above 1 kΩ; at least above 100Ω. The voltage should be smaller than 100 Volts but large enough that the current densities during the pulses are comparable to the current densities in the future operation of the component. Beyond this, care must be taken that the peak current intensities are large enough that the current expansion in the wafer 2 is limited by the cross-conductivity in the wafer 2. In particular, the lateral current expanse is smaller the larger the current through the component is.

It is noted that in the measuring probe 3 represented in FIG. 6, a contact pin 47 which is connected to a d.c. source is disposed next to the measuring device and pressed to the wafer 2 by spring power. The contact pin 47 serves for analyzing the aging behavior of the components on the wafer 2. To this end, first the optical characteristics of the component are analyzed by the measuring device 6. Next, the measuring probe 3 is displaced such that the contact pin 47 makes contact with the contact surface of the wafer 2. The contact pin 47 is then charged with a d.c. voltage signal, by which the component is artificially aged. Next, the measuring probe 3 is returned to its original position, and the optical characteristics of the component are measured again.

A current pulse transformer 49 is additionally disposed at the signal line 43 for measuring purposes. The pulsed-current transformer 49 serves for deriving, from the voltage signal, a current measuring signal which is needed for determining the efficiency of a component that is realized on the wafer. For opto-electronic components in particular, the current measurement is necessary in order to determine the efficiency of the component. But the current can also be measured by way of the voltage drop at the dropping resistor 42 or by way of a measuring resistance, which is not represented but which typically has a value of 1Ω. The measuring resistor is preferably arranged in the line 20 in place of the pulsed-current transformer 49, because a measuring signal with ground reference is generally advantageous.

In the operation of the pulsed-current source 7, transistor 45 is initially open, and the coupling capacitor 41 is charging. In order to release the current pulse, the transistor 45 is closed. A pulse signal whose trailing edge is determined by the time constant τ=RC is consequently emitted via the dropping resistor 42 to the carrier 1.

Figure 7:
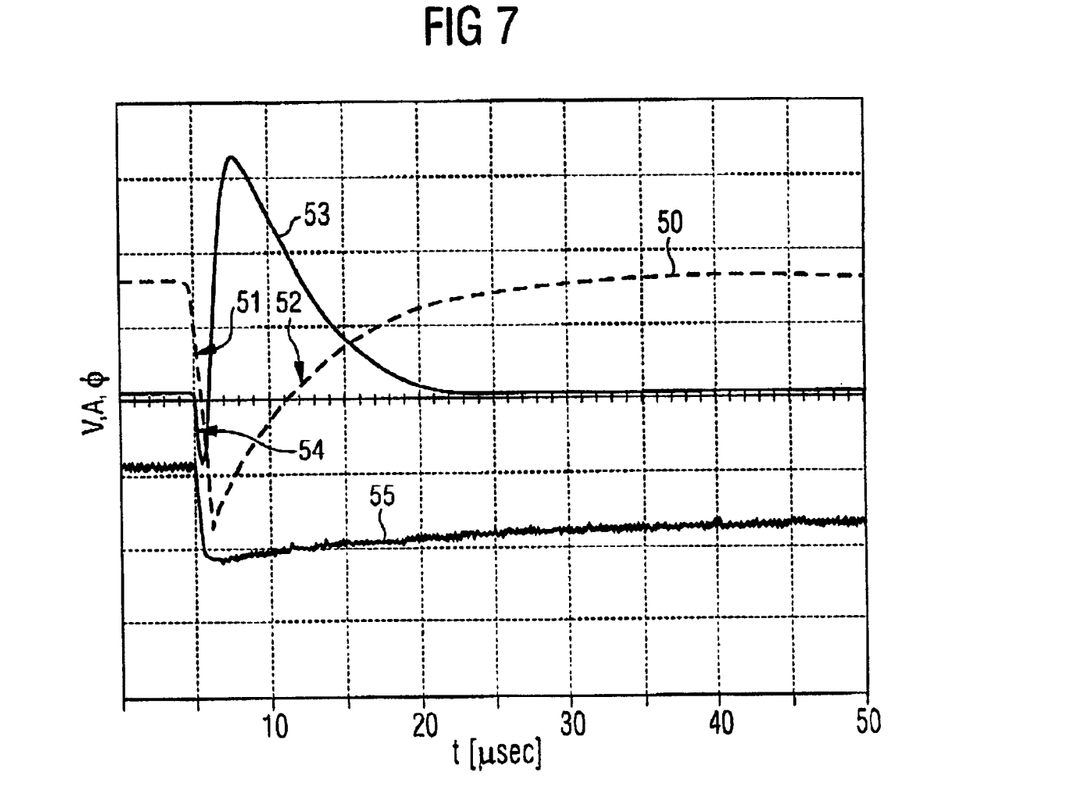
FIG. 7: a diagram with current, voltage, and detector measurement curves.

A current measurement curve 50 in FIG. 7 represents the behavior of the current pulse. One notes a steep rise 51 followed by the trailing edge 52, for which the time constant is τ=RC. A detector signal 53 of the detector 9 also has approximately this time constant.

It is noted that an undershoot 54 occurs at the start of the detector signal 53 due to cross-talk of the current pulse on the lines 43 and 20 onto the electronics of the detector 16.

Of further significance is a voltage measurement curve 55, which exhibits a substantially more gradual decline than the current measurement curve 50 and the detector signal 53. This is due on one hand to a diode structure which is realized in the contact body 11 in the unique instance being measured here, and on the other hand to the polarization of the electrolyte that has been poured in the recess 24. To this extent, an accumulator effect is apparent. The gradual decline of the voltage measurement curve 55 indicates that what is important is to send short pulses to the contact body 11. The pulse period should typically be between 0.1 μs and 1 ms. The interval between individual pulses should be longer than 1 ms.

Besides the particularly simple circuit for current pulse generation herein described, other high-voltage pulse generators can be utilized in connection with the dropping resistor 42.

Figure 8:
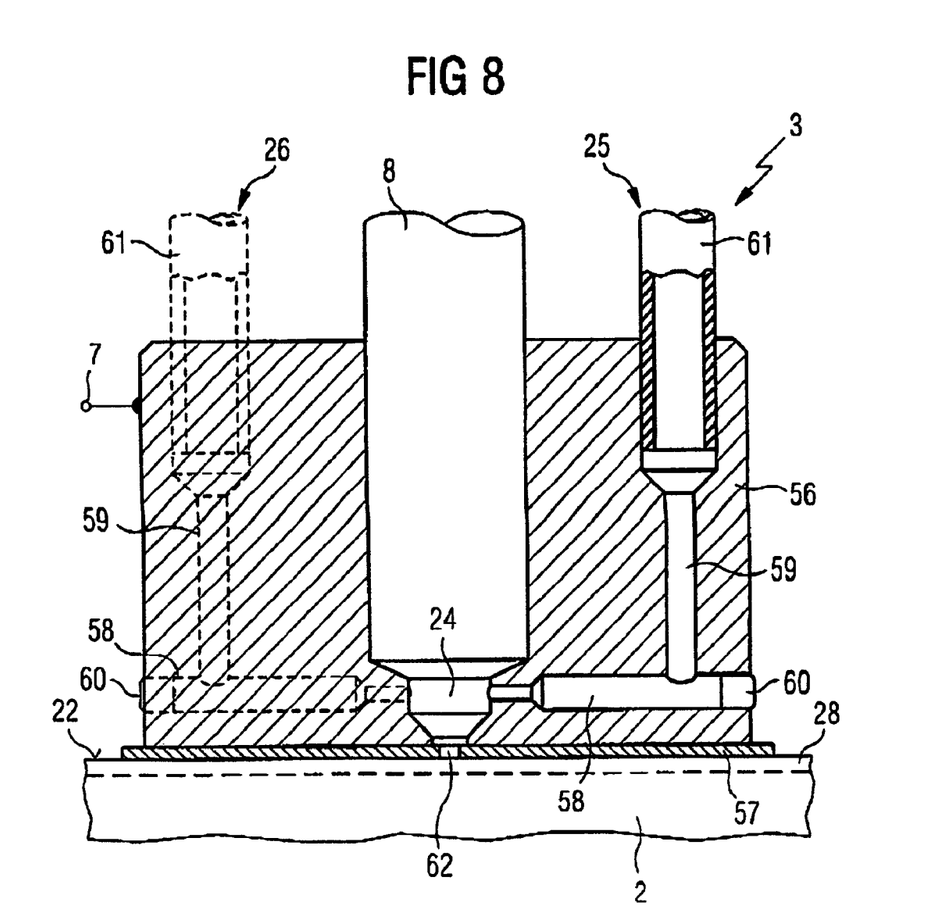
FIG. 8: a cross-sectional view through a particularly simple modified measuring probe.

Lastly, FIG. 8 represents a cross-section through an additional measuring probe 3, which is distinguished by its particularly simple construction. Instead of the plastic body 29, the measuring probe 3 represented in FIG. 8 has a metal body 56, which is electrically isolated from the underlying wafer 2 by a thin insulating plate 57. The recess 24 is limited above by the optical fiber 8. In the measuring probe 3 represented in FIG. 8, because the metal body 56 itself is connected to the pulsed-current source 7 directly, the metal body 56 itself acts as a probe contact by way of which the current is fed into the electrolyte in the recess 24.

In order to feed the electrolyte into the measuring probe, a supply line 25 and optionally a drain line 26 are provided. The supply line 25 and the optional drain line 26 are formed by transverse boreholes 58 and longitudinal boreholes 59, respectively. The transverse boreholes 58 are installed in the measuring probe 3 laterally and open into the recess 25. The transverse boreholes 58 are sealed on the outside by stoppers 60. The longitudinal boreholes 59, which open into the transverse boreholes 58, ultimately lead to tubes 61, which form the supply line 25 and the optional drain line 26.

In the measuring probe 3 from FIG. 8, the current is fed into the electrolytes in the recess 24 via the metal body 56. From there, the current goes through an opening 62 in the insulating plate 57, which is likewise filled with electrolyte, to the surface 22 of the wafer 2. Thus, the measuring probe 3 does not require a separate contact body consisting of SiC or some other transparent conductive material.

In addition, in the measuring probe 3 the recess 24 is filled prior to each measurement procedure by the pressing of electrolyte back through the supply line 25. In this technique, after the measuring probe is placed on, excess electrolyte is displaced to the surface 22 of the wafer 2 via unsealed points between the measuring probe 3 and the surface 22 of the wafer 2. If the optional drain line 26 is provided, the electrolyte 26 [sic] can of course be drained through the drain line 26 before the measuring probe 3 is taken off. It would also be imaginable both to supply the electrolytes and to extract them by way of the supply line 25. In this case, the measuring probe 3 has a particularly small design.

We claim:

1. Method for measuring product parameters of component on a wafer whereby, with the aid of a measuring probe which is placed on a wafer contact region, the component is charged with an electrical signal from a probe contact, which comprises achieving the electrical connection between the wafer and the measuring probe with the aid of an electrolyte which is inserted between the wafer contact region and the probe contact, the probe contact being a probe body formed of a conductive transparent material.

2. Method as claimed in claim 1, wherein a device for detecting the radiation emitted by the component is disposed on the side of the probe body that is averted from the wafer.

3. Method as claimed in claim 2, wherein the radiation is detected directly by a detector.

4. Method as claimed in claim 2, wherein the radiation is guided to a detector with the aid of an optical fiber.

5. Method as claimed in claim 1, wherein a probe body with a feed-through is utilized for the probe contact.

6. Method as claimed in claim 5, wherein the probe contact is formed by a tube with optical fibers inserted into it.

7. Method according to claim 1, wherein the signal is generated by a pulsed-current source.

8. Method according to claim 1, wherein the electrical signal comprises a series of single pulses or a series of pulse sequences which occur at intervals, whereby the single pulses or pulse sequences have a total charge of less than 1 mAs.

9. Method according to claim 1, wherein the electrolyte is located in a hollow space between the wafer end the measuring probe during the measurement procedure.

10. Method as claimed in claim 9, wherein prior to the measurement procedure, the electrolyte is introduced into the hollow space (24) via a supply line (25, 37).

11. Method according to claim 1, wherein the electrolyte is removed after the measurement procedure by way of a drain line.

12. Method according to claim 1, wherein after the component is measured with the aid of the measuring probe, a springing metal point-contact is placed on the wafer contact region, via which the component is charged with an ESD pulse; and that the component is then re-measured with the measuring probe.

13. Device for measuring product parameters of a component on a wafer, comprising a measuring probe on whose contact side a probe contact which is chargeable with an electrical signal is disposed, the probe contact is set back from the contact side; the probe contact is a probe body formed of a conductive transparent material; and a recess which is fillable with an electrolyte is so constructed on the contact side of the measuring probe that it extends to the probe contact.

14. Device as claimed in claim 13, wherein a detector for detecting the radiation emitted by the component is disposed on the side of the probe body which is averted from the recess.

15. Device as claimed in claim 13, wherein the probe contact is formed by a probe body (31) which includes a feed-through.

16. Device as claimed in claim 15, wherein in that the probe body is a tube (31) with optical fibers inserted into it.

17. Device according to claim 13, wherein the probe contact is connected to a pulsed-current source.

18. Device according to claim 13, wherein a springing metal contact point is disposed next to the measuring probe.

19. Device for measuring product parameters of a component on a wafer comprising:

a measuring probe on whose contact side a probe contact which is chargeable with an electrical signal is disposed, wherein the probe contact is set back from the contact side;

a recess which is fillable with an electrolyte is so constructed on the contact side of the measuring probe that it extends to the probe contact; and an optical fiber is disposed behind a side of the probe body averted from the recess for guiding the radiation emitted by the component to a detector.

20. Device for measuring product parameters of a component on a wafer comprising:

a measuring probe on whose contact side a probe contact which is chargeable with an electrical signal is disposed, wherein the probe contact is set back from the contact side;

a recess which is fillable with an electrolyte is so constructed on the contact side of the measuring probe that it extends to the probe contact; and a means of detecting the radiation emitted by the component is provided in the device at a position opposite the measuring probe.

* * * * *

UNITED STATES PATENT AND TRADEMARK OFFICE
CERTIFICATE OF CORRECTION

PATENT NO. : 6,946,864 B2 Page 1 of 1
DATED : September 20, 2005
INVENTOR(S) : Wolfgang Gramann et al.

It is certified that error appears in the above-identified patent and that said Letters Patent is hereby corrected as shown below:

<u>Column 7,</u>
Lines 6 and 7, claim 1 should read as follows:
 1. Method for measuring product parameters of components on a wafer whereby, with the aid of a measuring probe.

Signed and Sealed this

Twenty-eighth Day of March, 2006

JON W. DUDAS
*Director of the United States Patent and Trademark Office*